(12) United States Patent
Harada

(10) Patent No.: US 10,199,280 B2
(45) Date of Patent: Feb. 5, 2019

(54) METHOD FOR DETECTING BONDING FAILURE PART AND INSPECTION SYSTEM

(71) Applicant: SHIN-ETSU HANDOTAI CO., LTD., Tokyo (JP)

(72) Inventor: Kei Harada, Annaka (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 28 days.

(21) Appl. No.: 15/509,345

(22) PCT Filed: Aug. 31, 2015

(86) PCT No.: PCT/JP2015/004394
§ 371 (c)(1),
(2) Date: Mar. 7, 2017

(87) PCT Pub. No.: WO2016/051660
PCT Pub. Date: Apr. 7, 2016

(65) Prior Publication Data
US 2017/0278758 A1    Sep. 28, 2017

(30) Foreign Application Priority Data

Oct. 1, 2014 (JP) ................................ 2014-202740

(51) Int. Cl.
*G06K 9/00* (2006.01)
*H01L 21/66* (2006.01)
(Continued)

(52) U.S. Cl.
CPC ............. *H01L 22/12* (2013.01); *G01N 21/88* (2013.01); *G01N 21/9505* (2013.01);
(Continued)

(58) Field of Classification Search
USPC ....................................................... 382/150
See application file for complete search history.

(56) References Cited

U.S. PATENT DOCUMENTS 6,236,044 B1 * 5/2001 Chou ................. G01N 21/8806
                                                                    250/330
7,355,691 B2    4/2008 Yamaguchi et al.
(Continued)

FOREIGN PATENT DOCUMENTS

CN        103477212 A      12/2013
CN        104849281   *    8/2015  ............. G01N 21/28
(Continued)

OTHER PUBLICATIONS

Aug. 1, 2017 Office Action issued in Japanese Patent Application No. 2014-202740.
(Continued)

*Primary Examiner* — Jerome Grant, II
(74) *Attorney, Agent, or Firm* — Oliff PLC

(57) ABSTRACT

According to the present invention, there is provided a method for detecting a bonding failure part of a compound semiconductor chip cut from a compound semiconductor wafer in which a first transparent substrate composed of a compound semiconductor having a light-emitting layer is bonded with a second transparent substrate composed of a compound semiconductor, including irradiating the compound semiconductor chip with a coaxial vertical light, and identifying a color of a reflected-light from the bonding failure part of the compound semiconductor chip to detect the bonding failure part. As a result, it is possible, to provide a method for detecting a bonding failure part which can precisely detect a bonding failure part on a bonding interface of a compound semiconductor chip cut from a compound semiconductor wafer in which two transparent substrates composed of a compound semiconductor are directly bonded with each other.

16 Claims, 3 Drawing Sheets

(51) Int. Cl.
| | |
|---|---|
| *H01L 33/00* | (2010.01) |
| *G01N 21/88* | (2006.01) |
| *H01L 21/68* | (2006.01) |
| *H01L 21/683* | (2006.01) |
| *H01L 23/00* | (2006.01) |
| *H01L 27/146* | (2006.01) |
| *G01N 21/95* | (2006.01) |
| *G06T 7/00* | (2017.01) |
| *G01N 21/84* | (2006.01) |

(52) U.S. Cl.
CPC .......... *G06T 7/0004* (2013.01); *H01L 21/681* (2013.01); *H01L 21/6836* (2013.01); *H01L 22/20* (2013.01); *H01L 24/78* (2013.01); *H01L 24/85* (2013.01); *H01L 27/14636* (2013.01); *H01L 33/00* (2013.01); *G01N 2021/8438* (2013.01); *G06T 2207/30152* (2013.01); *H01L 2221/68327* (2013.01)

(56) References Cited

U.S. PATENT DOCUMENTS

| | | | |
|---|---|---|---|
| 9,244,020 B2 | 1/2016 | Leconte et al. | |
| 2006/0029257 A1* | 2/2006 | Eguchi | G06T 7/0004 382/108 |
| 2010/0309309 A1* | 12/2010 | Bing | G01B 11/046 348/128 |
| 2012/0307236 A1* | 12/2012 | Ortner | G01N 21/9505 356/239.3 |
| 2014/0170769 A1* | 6/2014 | Chung | G01N 21/6428 436/501 |
| 2014/0335761 A1* | 11/2014 | Chou | B24B 49/12 451/5 |
| 2016/0013368 A1* | 1/2016 | Goto | H01L 33/501 257/98 |
| 2017/0135583 A1* | 5/2017 | Blodgett | A61B 5/0066 |
| 2017/0278758 A1* | 9/2017 | Harada | H01L 22/12 |
| 2017/0370855 A1* | 12/2017 | Takahashi | G01N 33/381 |

FOREIGN PATENT DOCUMENTS

| | | | | |
|---|---|---|---|---|
| EP | 1835495 | * | 9/2007 | .............. G01B 7/09 |
| JP | 2009-021572 A | | 1/2009 | |
| JP | 2009-288110 A | | 12/2009 | |
| JP | 2013-104860 A | | 5/2013 | |
| JP | 2014-126436 A | | 7/2014 | |
| JP | 006121758 | * | 4/2017 | .......... G01N 21/958 |
| TW | 200734630 A | | 9/2007 | |

OTHER PUBLICATIONS

Apr. 4, 2017 International Preliminary Report on Patentability issued in International Patent Application No. PCT/JP2015/004394.
Oct. 27, 2015 International Search Report issued in International Patent Application No. PCT/JP2015/004394.
Apr. 24, 2018 Office Action issued in Chinese Application No. 201580047982.2.
Jan. 12, 2018 Taiwanese Office Action and Search Report issued in Application No. 104129248.

* cited by examiner (a) Taken image under ring illumination (b) Taken image in Example

METHOD FOR DETECTING BONDING FAILURE PART AND INSPECTION SYSTEM

TECHNICAL FIELD

The present invention relates to a method for detecting a bonding failure part and an inspection system of performing this detection method.

BACKGROUND ART

Ultra-high luminance light-emitting devices are produced by successively growing a quaternary light-emitting layer and a light-extraction window layer on a GaAs substrate in a reactor using a Metal Organic Vapor Phase Epitaxy method (hereinafter, referred to as a MOVPE method), and growing a thicker window layer on the window layer after transferring the substrate into a reactor using a Hydride Vapor Phase Epitaxy method (hereinafter, referred to as a HVPE method), followed by performing processes such as electrode formation, and cutting it into individual chips through a dicing step, etc. Such a thickening of the window layer improves a light extraction efficiency from the side of the light-emitting device.

On the other hand, a light emitted from the light-emitting layer toward the substrate side is absorbed by the GaAs substrate. Accordingly, in order to improve the light extraction efficiency, the GaAs substrate is removed by etching to directly bond an epitaxial wafer in which the growth substrate is removed and a GaP substrate or a sapphire substrate, which is a transparent substrate, so as to prevent the foregoing absorption of light from the light emitting layer and so as to extract the light emitted from the light emitting layer toward the substrate side. Such a structure makes it possible to efficiently extract the light from the light emitting layer through the upper window layer and the transparent substrate which is bonded directly thereto.

In bonding by direct joining, however, a region having a void formed therein (a bonding failure part) is sometimes observed on the bonding interface. There are many automatic detectors using an optical system for detecting such a bonding failure part (for example, see Patent Document 1). In these detectors, however, an illumination light is irradiated from the horizontal direction or the upper diagonal direction, and the bonding failure part is detected on the basis of the difference of brightness (light and darkness) between the reflected-light from the bonding failure part and the reflected-light from the bonding good part.

CITATION LIST

Patent Literature

Patent Document 1: Japanese Unexamined Patent publication (Kokai) No. 2009-021572

SUMMARY OF INVENTION

Problem to be Solved by the Invention

In the detection method described above, however, it is difficult to detect the bonding failure part with high precision, and it has been necessary to rely on visual inspection, which are costly, since there is a small difference of brightness (light and darkness) between the reflected-light from the bonding failure part and that from the bonding good part. Incidentally, in a visual inspection step, the bonding failure part is detected by visual inspection using a stereoscopic microscope (under LED illumination), and failed chips are removed with vacuum tweezers and so on. The cost of such a visual inspection step holds heavy weight in the production steps. Moreover, in the visual inspection step, the detection precision often uncertain and unstable, and there is a problem that the visual inspection have to be performed multiply, not only one time.

The present invention was accomplished to solve the above-described problems. It is an object of the present invention to provide a method for detecting a bonding failure part which can precisely detect a bonding failure part on a bonding interface of a compound semiconductor chip cut from a compound semiconductor wafer in which two transparent substrates each composed of a compound semiconductor are bonded with each other by direct joining.

Means for Solving Problem

To solve the problems, the present invention provides a method for detecting a bonding failure part of a compound semiconductor chip cut from a compound semiconductor wafer in which a first transparent substrate composed of a compound semiconductor having a light-emitting layer is bonded with a second transparent substrate composed of a compound semiconductor, comprising:
  irradiating the compound semiconductor chip with a coaxial vertical light, and
  identifying a color of a reflected-light from the bonding failure part of the compound semiconductor chip to detect the bonding failure part.

By irradiating the compound semiconductor chip with a coaxial vertical light, and identifying a color of a reflected-light from the bonding failure part of the compound semiconductor chip to detect the bonding failure part as described above, it is possible to precisely detect the bonding failure part on the bonding interface of the compound semiconductor chip, and to reduce the cost of the inspection step since visual inspection is not necessary.

It is preferable that the coaxial vertical light includes a wavelength band of 580 nm to 610 nm, and the coaxial vertical light has an illuminance of 40000 lux or more.

If the coaxial vertical light includes a wavelength band of 580 nm to 610 nm, the bonding failure part can be securely detected. The coaxial vertical light having an illuminance of 40000 lux or more makes it possible to obtain more information from the bonding interface, and to detect the bonding failure part more securely.

In identifying the color of a reflected-light from the bonding failure part, the following stages can be included:
  capturing an image of the compound semiconductor chip,
  extracting a previously registered color from the captured image,
  subjecting the captured image to gray conversion to make the extracted color be white and other colors be gray, and
  performing binarization processing of the image subjected to the gray conversion.

The method described above can be suitably used as the method for identifying a reflected-light from a bonding failure part.

In identifying the color of a reflected-light from the bonding failure part, it is preferable to include identifying a color of a wavelength band of 580 nm to 610 nm.

By identifying a color of the wavelength band described above, it is possible to securely identify a color of a reflected-light from a bonding failure part.

The present invention also provides an inspection system of performing the method for detecting a bonding failure part, comprising:

a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

The inspection system with such a structure can be suitably used as an inspection system of performing the method for detecting a bonding failure part of the present invention.

Effect of Invention

As described above, according to the present invention, it is possible to precisely detect a bonding failure part on a bonding interface of a compound semiconductor chip, and to reduce the cost of an inspection step since visual inspection is not necessary.

DESCRIPTION OF EMBODIMENTS

Figure 1:
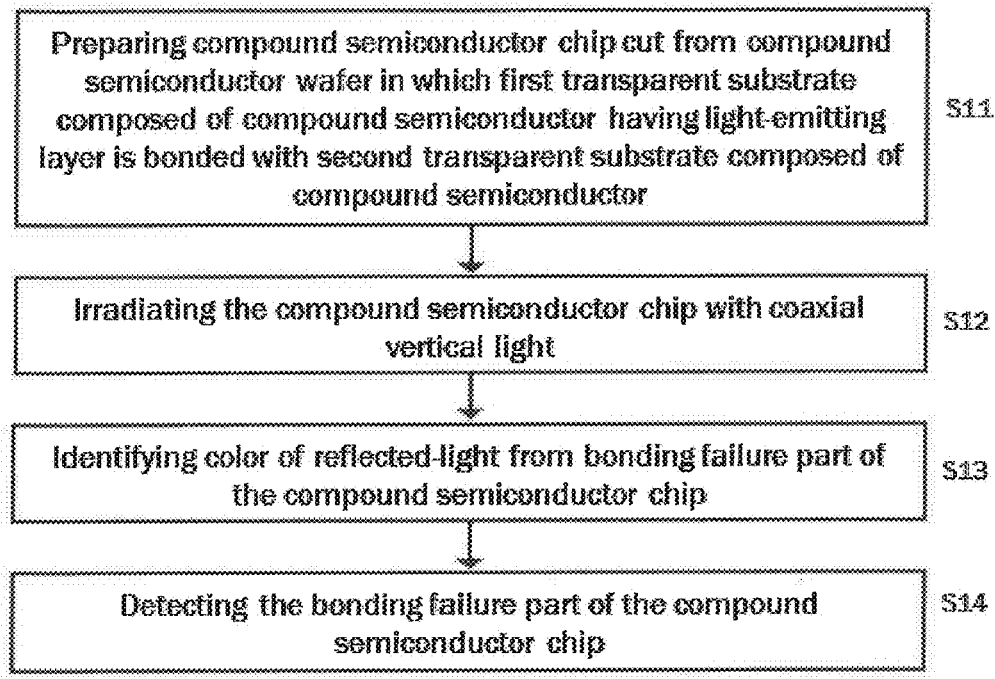
FIG. 1 is a flowchart of a method for detecting a bonding failure part of the present invention.

Hereinafter, the present invention will be specifically described with reference to FIGS. as an example of the embodiments, but the present invention is not limited thereto.

As described above, in manufacturing an ultra-high luminance light-emitting device, it has been performed direct joining of an epitaxial wafer in which the growth substrate is removed and a GaP substrate or a sapphire substrate, which is a transparent substrate, so as to make it possible to extract light from the light-emitting layer efficiently. In bonding by direct joining, however, a bonding failure part is sometimes observed on the bonding interface. There are many automatic detectors using an optical system for detecting such a bonding failure part. In these detectors, an illumination light is irradiated from the horizontal direction or the upper diagonal direction, and the bonding failure part is detected on the basis of the difference of brightness (light and darkness) between the reflected-light from the bonding failure part and the reflected-light from the bonding good part.

In the detection method described above, however, it is difficult to detect the bonding failure part with high precision, and it has been necessary to rely on visual inspection, which are costly.

Accordingly, the present inventor has diligently investigated on a method for detecting a bonding failure part which can precisely detect a bonding failure part on a bonding interface of a compound semiconductor chip cut from a compound semiconductor wafer in which two transparent substrates composed of a compound semiconductor are bonded with each other by direct joining. As a result, the present inventor has found that the bonding failure part on the bonding interface of the compound semiconductor chip can be precisely detected by irradiating the compound semiconductor chip with a coaxial vertical light, and identifying a color of a reflected-light from the bonding failure part of the compound semiconductor chip to detect the bonding failure part; thereby brought the present invention to completion.

Herein, the defect of a compound semiconductor substrate to be inspected and defect inspection will be described. The compound semiconductor substrate to be inspected can be a compound semiconductor substrate in which an n-type cladding layer with a thickness of about 1 μm, an active layer with a thickness of about 0.6 μm, and a p-type cladding layer with a thickness of about 1 μm each composed of $(Al_xGa_{1-x})_yIn_{1-y}P$ are epitaxially grown by a MOCVD in this order as a light-emitting layer part on an n-type GaAs single crystal substrate; and a current diffusion layer (a window layer) composed of a p-type GaP is formed thereon by a HVP method; with the GaAs single crystal substrate being removed from this substrate, and a transparent n-type GaP substrate or sapphire substrate being directly joined onto the surface where the GaAs single crystal substrate is removed, for example. The joined surface thereof sometimes contains a bonding failure part such as a void and a micro void. They are transferred to a chip forming step while remaining these bonding failure part being contained. And the chips containing a bonding failure part described above is removed in a visual inspection in the process or a finishing inspection (an inspection of a chip attached with electrodes).

First, an example of the inventive inspection system will be described with reference to FIGS. 3 to 4.

Figure 3:
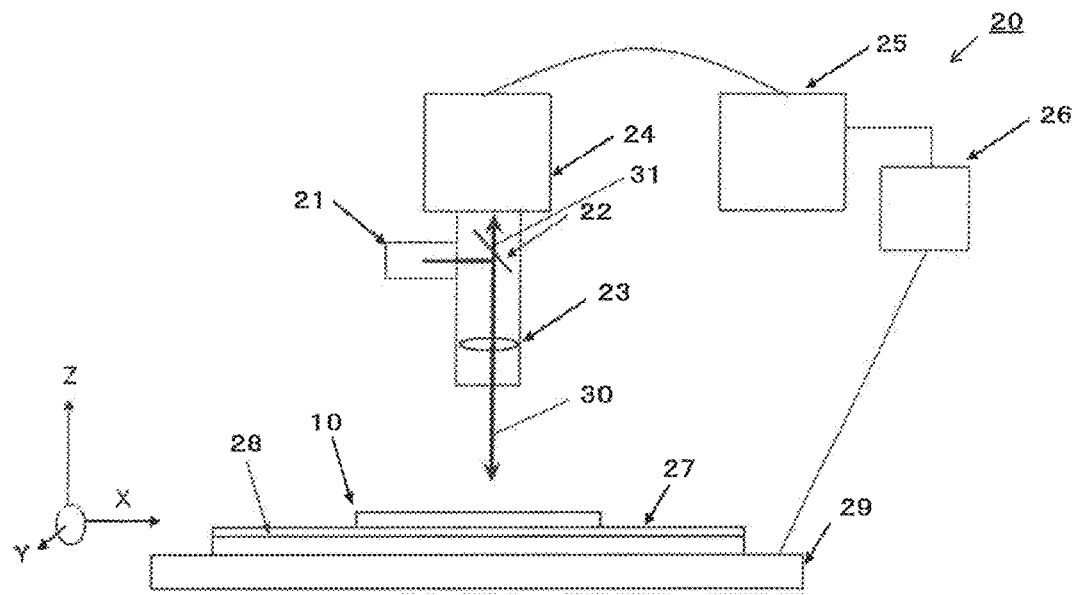
FIG. 3 is a diagram showing an example of a structure of an inspection system of the present invention.

The inspection system 20 in FIG. 3 is provided with a coaxial vertical lighting device 21 for irradiating a workpiece (an inspection object) 10 with a light (an illumination light) 30, a work frame (a mount) 28 for mounting the workpiece 10, an X-Y stage 29 for carrying the work frame 28, an imaging device 24 for taking an image of a reflected-light 31 from the workpiece 10, a controller for controlling drive of the X-Y stage 29, and an image processor for performing image processing of the image taken with the imaging device 24. The workpiece 10 can be irradiated with the light from the coaxial vertical lighting device 21 through a half-mirror 22 and a lens 23, for example. The workpiece 10 can be fixed onto the work frame 28 with a tape 27 for holding a workpiece, for example. As the controller and the image processor, a personal computer 26 can be used, for example. The inspection system 20 can also have a monitor 25 for displaying images taken with the imaging device 24 and images processed with the image processor.

The enlarged view of a workpiece 10 is shown in FIG. 4(a). The workpiece 10 is cut by dicing, etc. from a wafer in which the first transparent substrate 13 in which a light-emitting layer 11 and a window layer 12 are laminated is bonded with the second transparent substrate 14, and electrodes 15 are formed. The light-emitting layer 11 is a quaternary light-emitting layer composed of $(Al_xGa_{1-x})_yIn_{1-y}P$, for example; the window layer 12 is a GaP layer, for example; and the second transparent substrate 14 is a GaP substrate or a sapphire substrate, for example.

On the bonding interface of the first transparent substrate 13 and the second transparent substrate 14 of the workpiece 10, there sometimes arises a bonding failure part 16 such as a void and a micro void.

FIG. 4(b) shows an image taken with the imaging device 24, and FIG. 4(c) shows an image in which the image of FIG. 4(b) is processed with the image processor.

Then, the inventive method for detecting a bonding failure part will be described with reference to FIGS. 1 to 2.

First, a compound semiconductor chip cut from a compound semiconductor wafer in which the first transparent substrate composed of a compound semiconductor having a light-emitting layer is bonded with the second transparent substrate composed of a compound semiconductor into individual pieces, is prepared (see Step S11 in FIG. 1).

Specifically, the first transparent substrate 13 in which the light-emitting layer 11 and the window layer 12 are laminated is bonded with the second transparent substrate 14, and the electrodes 15 are formed thereon. This wafer is cut into individual workpieces 10 by dicing and so on (see FIG. 4(a)). This workpieces 10 is mounted on the work frame 28 of the inspection system 20 (see FIG. 3).

Incidentally, the workpieces 10 is a wafer after dicing, and can be an aggregate of chips before the chips cut into individual pieces are picked up from a dicing tape.

Then, the compound semiconductor chip is irradiated with a coaxial vertical light (see Step S12 in FIG. 1).

Specifically, the workpiece 10 is irradiated with the light 30 from the coaxial vertical lighting device 21 almost vertically through the half-mirror 22 and the lens 23 (see FIG. 3, FIG. 4(a)).

The light 30 from the coaxial vertical lighting device 21 preferably includes a wavelength band of 580 nm to 610 nm. The light with such a wavelength is suitable for detecting a bonding failure part. Because a light with a long wavelength such as a red light (620 to 750 nm) is liable to detect information of deep parts, and increases noises accordingly; on the other hand, a light with a short wavelength such as a blue light (450 to 495 nm) increases information of the surface, and increases noises accordingly.

It is to be noted that, irradiating a ring illumination light increases noises, and cannot identify a defective part and a good part properly.

The illuminance of the light 30 from the coaxial vertical lighting device 21, which is not particularly limited, is preferably 40000 lux or more. Having an illuminance in such a range, it is possible to obtain more information from a bonding interface, and to detect a bonding failure part more securely. When the illuminance is low, the color development from a defect part becomes dull, and a bonding failure part cannot be detected properly; and when the illuminance is too high, the color development from the surface becomes strong, which can be noises.

In order not to pick extra noises, it is preferable to use a lens with a shallow depth of a focus as the lens 23.

Then, a color of a reflected-light from the bonding failure part of the compound semiconductor chip is identified (see Step S13 in FIG. 1).

Figure 4:
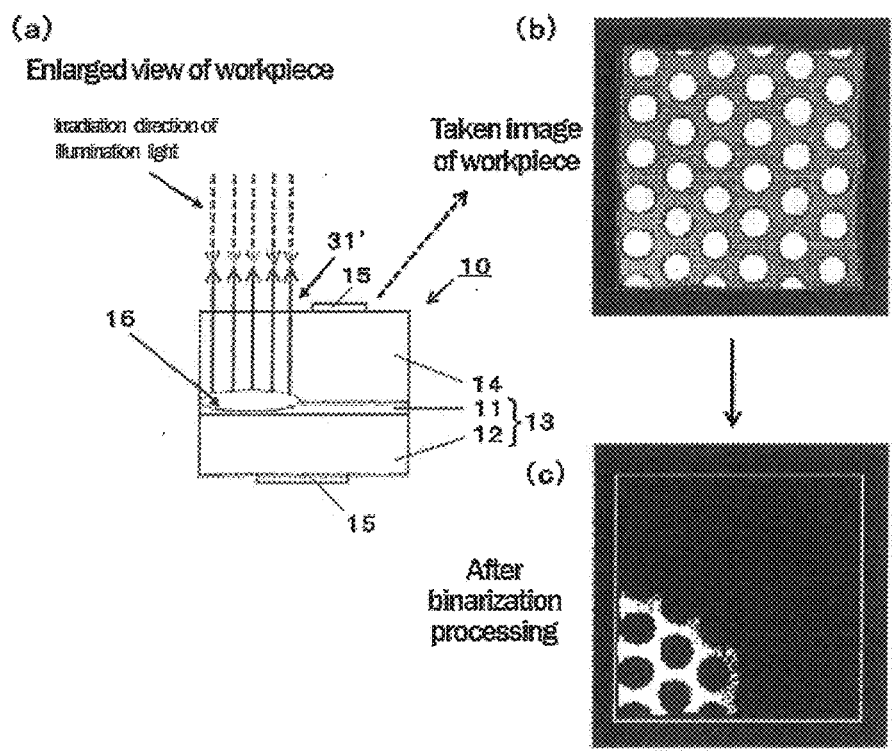
FIG. 4 represent an enlarged view of a workpiece (an inspection object) to be inspected by an inspection system of the present invention, a taken image of the workpiece, and a diagram showing an image of the taken image after being subjected to gray conversion and binarization processing.

Specifically, a reflected-light 31 from the workpiece 10 is captured to the imaging device 24 through the lens 23 and the half-mirror 22 to detect whether a reflected-light 31' from the bonding failure part 16 (see FIG. 4 (a)) is contained in the reflected-light 31 or not by identifying a color of the reflected-light 31' from the bonding failure part 16.

Figure 2:
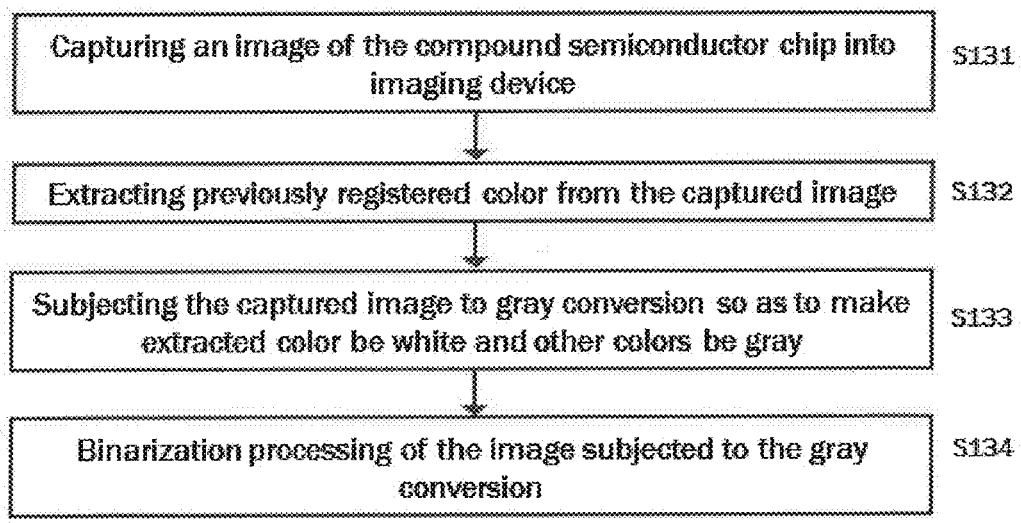
FIG. 2 is a flowchart showing an example of the step S 13 of a method for detecting a bonding failure part of the present invention.

Herein, an example of a process performed in Step S13 in FIG. 1 is shown in the flowchart of FIG. 2.

First, an image of the compound semiconductor chip is captured to the imaging device (see Step S131 in FIG. 2).

Specifically, the image of the workpiece 10 is captured to the imaging device 24 by capturing the reflected-light 31 from the workpiece 10 to the imaging device 24 through the lens 23 and the half-mirror 22. An example of an image thus captured into the imaging device 24 is shown in FIG. 4(b).

Then, a previously registered color is extracted from the captured image (see Step S132 in FIG. 2).

Specifically, the previously registered color is extracted from the image captured to the imaging device 24 in Step S131 with an image processor (e.g., the personal computer 26 (see FIG. 3)).

It is preferable to select a color of a wavelength band of 580 nm to 610 nm as the color to be registered. When the color to be registered is set to the color having the wavelength band described above, it is possible to securely identify a color of a reflected-light from a bonding failure part.

Subsequently, the captured image is subjected to gray conversion to make the extracted color be white and other colors be gray (see Step S133 in FIG. 2).

Specifically, the image captured into the imaging device 24 in Step S131 is subjected to gray conversion so as to make the color extracted in Step S132 be white and other colors be gray by using an image processor (e.g., the personal computer 26).

Such a procedure gives an image in which regions corresponding to the bonding failure part 16 is white, and the region without causing bonding failure is gray (i.e., an image subjected to gray conversion).

Then, binarization processing is performed on the image subjected to the gray conversion (see Step S134 in FIG. 2).

Specifically, the image subjected to the gray conversion in Step S133 is subjected to binarization processing with an image processor (e.g., the personal computer 26).

Such a procedure gives an image in which regions corresponding to the bonding failure part 16 is white, and the region without causing bonding failure is black (i.e., an image subjected to binarization processing). An example of an image subjected to binarization processing is shown in FIG. 4 (c)).

It is also possible to perform filtering processing to the image subjected to binarization processing with an image processor (e.g., the personal computer 26) to remove noise, etc. if it is necessary.

Subsequently, returning to the flowchart of FIG. 1 again, the bonding failure part of the compound semiconductor chip is detected (see Step S14 in FIG. 1).

Specifically, an existence of a bonding failure part is determined on the basis of the area and the number of white regions in the image subjected to binarization processing obtained in Step S134. This determination can be performed by using the personal computer 26 (see FIG. 3).

The inventive method for detecting a bonding failure part described above makes it possible to precisely detect a bonding failure part on a bonding interface of a compound semiconductor chip, and to reduce the cost of an inspection step since visual inspection is not necessary.

The inventive inspection system described above can suitably perform the method for detecting a bonding failure part of the present invention.

EXAMPLES

The present invention will be specifically described below with reference to Example and Comparative Example, but the present invention is not limited to thereto.

Example

On a wafer with a diameter of 50 mm having a substrate (the first transparent substrate) 13 in which a window layer 12 composed of GaP had been epitaxially grown on a light-emitting layer 11 composed of AlGaInP and having a GaP substrate 14 bonded to the light-emitting layer side thereof, Au base ohmic electrodes 15 were formed on the p-type side and the n-type side thereof. Then, this was cut into individual pieces (chipping).

A workpiece 10, which was an aggregation of the cut chips before being picked up from a dicing tape, was adhered to a prescribed work frame 28. This was set to an inspection system 20 shown in FIG. 3, and inspected in accordance with the method described above, whereby failed chips were removed automatically. This was performed by using an imaging device 24 of a color camera of AT200 3CCD manufactured by JAI Ltd., a lens 23 of MML4-HR65DVI-5M manufactured by SCHOTT MORIX CORPORATION, and a coaxial vertical lighting device 21 of HLV2-22SW-3W manufactured by CCS Inc.

This inspection was performed on three species. Table 1 shows the numbers of chips which passed the inspection of Comparative example.

As a result, the method of Example detected failed chips even in the chips which passed in an inspection of Comparative Example described below as shown in Table 1, which revealed an advantage of the present invention.

Figure 5:
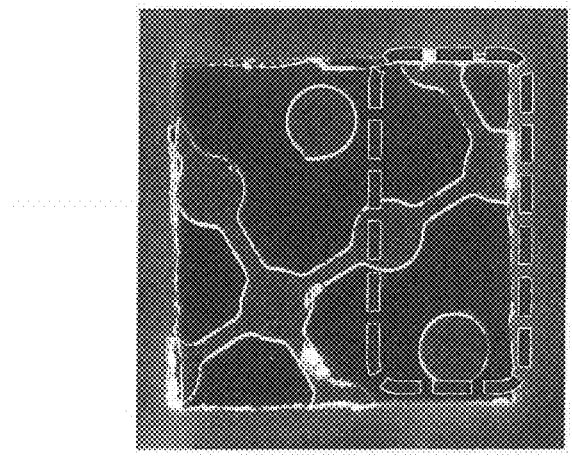
FIG. 5 are diagrams each showing an image of a chip which passed visual inspection and fail in Example, taken with a ring illumination device, and an image of the above-described chip taken in Example.
Figure 5:
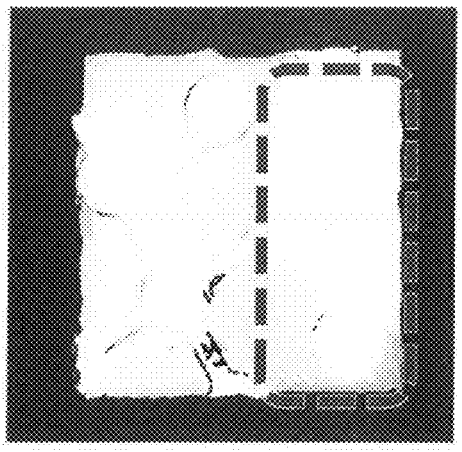

FIG. 5(a) shows an image of a chip which passed a visual inspection and failed in Example, taken with a ring illumination device, which have been used in conventional visual inspections. FIG. 5(b) shows an image of a chip which passed a visual inspection and failed in Example, taken by the method of Example. Incidentally, the areas surrounded by broken lines in FIG. 5(a) and FIG. 5(b) are regions where bonding failure were detected in inspection of Example.

It was found that bonding failure part can be detected more easily by extracting a previously registered color from a reflected-light from a workpiece irradiated with a coaxial vertical light. The time taken for the inspection could be reduced by about 70% compared to Comparative Example.

TABLE 1

| Species | Number of chips which passed inspection of Comparative Example | Number of chips in which failure was detected among chips which passed inspection of Comparative Example |
| --- | --- | --- |
| A | 31,084 | 12 |
| A | 30,147 | 10 |
| B | 12,452 | 5 |
| B | 15,621 | 3 |
| C | 29,422 | 8 |
| C | 28,158 | 6 |

Comparative Example

Visual inspections were carried out on the same chips in Example (three species of chips shown in Table 1).

As shown in Table 1, in all of three species, failures were detected in inspection of Example among the chips which passed inspection of Comparative Example. It was found that Comparative Example showed lower inspection precision compared to Example.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A method for detecting a bonding failure part of a compound semiconductor chip cut from a compound semiconductor wafer in which a first transparent substrate composed of a compound semiconductor having a light-emitting layer is bonded with a second transparent substrate composed of a compound semiconductor, comprising:
   irradiating the compound semiconductor chip with a coaxial vertical light, and
   identifying a color of a reflected-light from the bonding failure part of the compound semiconductor chip to detect the bonding failure part.

2. An inspection system of performing the method for detecting a bonding failure part according to claim 1, comprising:
   a coaxial vertical lighting device for irradiating an inspection object with a light,
   a mount for mounting the inspection object,
   an X-Y stage for carrying the mount,
   an imaging device for taking an image of a reflected-light from the inspection object,
   a controller for controlling drive of the X-Y stage, and
   an image processor for performing image processing of the image taken with the imaging device.

3. The method for detecting a bonding failure part according to claim 1, wherein said identifying a color of a reflected-light from the bonding failure part includes identifying a color of a wavelength band of 580 nm to 610 nm.

4. An inspection system of performing the method for detecting a bonding failure part according to claim 3, comprising:
   a coaxial vertical lighting device for irradiating an inspection object with a light,
   a mount for mounting the inspection object,
   an X-Y stage for carrying the mount,
   an imaging device for taking an image of a reflected-light from the inspection object,
   a controller for controlling drive of the X-Y stage, and
   an image processor for performing image processing of the image taken with the imaging device.

5. The method for detecting a bonding failure part according to claim 1, wherein said identifying a color of a reflected-light from the bonding failure part includes
   capturing an image of the compound semiconductor chip,
   extracting a previously registered color from the captured image,
   subjecting the captured image to gray conversion to make the extracted color be white and other colors be gray, and
   performing binarization processing of the image subjected to the gray conversion.

6. An inspection system of performing the method for detecting a bonding failure part according to claim 5, comprising:
   a coaxial vertical lighting device for irradiating an inspection object with a light,
   a mount for mounting the inspection object, an X-Y stage for carrying the mount,
an imaging device for taking an image of a reflected-light from the inspection object,
a controller for controlling drive of the X-Y stage, and
an image processor for performing image processing of the image taken with the imaging device.

7. The method for detecting a bonding failure part according to claim 5, wherein said identifying a color of a reflected-light from the bonding failure part includes identifying a color of a wavelength band of 580 nm to 610 nm.

8. An inspection system of performing the method for detecting a bonding failure part according to claim 7, comprising:
a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

9. The method for detecting a bonding failure part according to claim 1, wherein
the coaxial vertical light includes a wavelength band of 580 nm to 610 nm, and
the coaxial vertical light has an illuminance of 40000 lux or more.

10. The method for detecting a bonding failure part according to claim 9, wherein said identifying a color of a reflected-light from the bonding failure part includes identifying a color of a wavelength band of 580 nm to 610 nm.

11. An inspection system of performing the method for detecting a bonding failure part according to claim 10, comprising:
a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

12. The method for detecting a bonding failure part according to claim 9, wherein said identifying a color of a reflected-light from the bonding failure part includes
capturing an image of the compound semiconductor chip,
extracting a previously registered color from the captured image,
subjecting the captured image to gray conversion to make the extracted color be white and other colors be gray, and
performing binarization processing of the image subjected to the gray conversion.

13. The method for detecting a bonding failure part according to claim 12, wherein said identifying a color of a reflected-light from the bonding failure part includes identifying a color of a wavelength band of 580 nm to 610 nm.

14. An inspection system of performing the method for detecting a bonding failure part according to claim 13, comprising:
a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

15. An inspection system of performing the method for detecting a bonding failure part according to claim 12, comprising:
a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

16. An inspection system of performing the method for detecting a bonding failure part according to claim 9, comprising:
a coaxial vertical lighting device for irradiating an inspection object with a light,
a mount for mounting the inspection object,
an X-Y stage for carrying the mount,
an imaging device for taking an image of a reflected-light from the inspection object,
a controller for controlling drive of the X-Y stage, and
an image processor for performing image processing of the image taken with the imaging device.

* * * * *